(12) United States Patent
Senno et al.

(10) Patent No.: US 9,990,858 B2
(45) Date of Patent: Jun. 5, 2018

(54) GOLF SWING CLASSIFICATION METHOD, GOLF CLUB SELECTION METHOD, GOLF SWING CLASSIFICATION DEVICE, AND GOLF SWING CLASSIFICATION SYSTEM

(71) Applicants: BRIDGESTONE CORPORATION, Chuo-ku, Tokyo (JP); BRIDGESTONE SPORTS CO., LTD, Minato-ku, Tokyo (JP)

(72) Inventors: Yoshikazu Senno, Kodaira (JP); Koji Takao, Kodaira (JP); Daisuke Kondo, Kodaira (JP); Hideo Matsunaga, Chichibu (JP); Hirotada Iwade, Chichibu (JP)

(73) Assignees: BRIDGESTONE CORPORATION, Tokyo (JP); Bridgestone Sports Co., Ltd., Tokyo (JP)

( * ) Notice: Subject to any disclaimer, the term of this patent is extended or adjusted under 35 U.S.C. 154(b) by 313 days.

(21) Appl. No.: 14/289,094

(22) Filed: May 28, 2014

(65) Prior Publication Data
US 2014/0357393 A1    Dec. 4, 2014

(30) Foreign Application Priority Data

May 31, 2013 (JP) ................................. 2013-116370

(51) Int. Cl.
| | |
|---|---|
| *A63B 69/36* | (2006.01) |
| *G06F 19/00* | (2018.01) |
| *G09B 19/00* | (2006.01) |
| *G06K 9/00* | (2006.01) |

(Continued)

(52) U.S. Cl.
CPC ...... *G09B 19/0038* (2013.01); *G06K 9/00342* (2013.01); *G06K 9/00536* (2013.01); *G06T 7/248* (2017.01); *A61B 5/6895* (2013.01); *G06T 2207/10016* (2013.01);
(Continued)

(58) Field of Classification Search
CPC ...................................................... A63B 69/36
See application file for complete search history.

(56) References Cited

U.S. PATENT DOCUMENTS

| | | | | |
|---|---|---|---|---|
| 5,951,410 A | * | 9/1999 | Butler ............... | A63B 60/42 473/223 |
| 7,651,403 B2 | * | 1/2010 | Yamamoto ........ | A63B 24/0003 473/151 |
| 2003/0040380 A1 | | 2/2003 | Wright et al. | |

(Continued)

FOREIGN PATENT DOCUMENTS

| | | |
|---|---|---|
| CN | 101927084 A | 12/2010 |
| CN | 103071280 A | 5/2013 |

(Continued)

*Primary Examiner* — Dmitry Suhol
*Assistant Examiner* — Ankit Doshi
(74) *Attorney, Agent, or Firm* — Sughrue Mion, PLLC

(57) ABSTRACT

Provided is a golf swing classification method that is capable of optimizing selection of a golf club. A golf swing classification method when a golf club hits a golf ball according to the present invention includes the steps of: acquiring acceleration in at least a single point on the golf club or in at least one point that follows the single point during the golf swing; and mapping a behavior of the golf club based on a time period from a time point when an absolute value of the acceleration is at a maximum to a time point when the golf club hits the golf ball.

7 Claims, 4 Drawing Sheets

(51) Int. Cl.
*G06T 7/246* (2017.01)
*A61B 5/00* (2006.01)
(52) U.S. Cl.
CPC ............... *G06T 2207/10021* (2013.01); *G06T 2207/30204* (2013.01); *G06T 2207/30221* (2013.01)

(56) References Cited

U.S. PATENT DOCUMENTS

2010/0210371 A1* 8/2010 Sato et al. .................... 473/223
2014/0100050 A1* 4/2014 Ota .................... A63B 69/3632
 473/223

FOREIGN PATENT DOCUMENTS

| | | |
|---|---|---|
| JP | 2005074010 A | 3/2005 |
| JP | 4145618 B2 | 9/2008 |
| JP | 2009240677 A | 10/2009 |

* cited by examiner

GOLF SWING CLASSIFICATION METHOD, GOLF CLUB SELECTION METHOD, GOLF SWING CLASSIFICATION DEVICE, AND GOLF SWING CLASSIFICATION SYSTEM

TECHNICAL FIELD

The present invention relates to a golf swing classification method, a golf club selection method, a golf swing classification device, and a golf swing classification system.

BACKGROUND ART

When golfers swing a golf club, a behavior of the golf club is varied in accordance with force applied from the golfers to the golf club. Although golfers have different conditions for an ideal golf club, one condition of particular importance may be a high head speed of the golf club when the golfers swing the golf club. The reason is that the high head speed makes it possible to easily achieve a long flying distance.

Conventionally, as a method for selecting, for each golfer, a golf club that would increase the head speed, it has been proposed to calculate a deformed shape of a shaft included in a golf club during a swing of the golfer and grasp a feature of the swing of the golfer, and to subsequently select an optimal shaft for the golfer. (For example, refer to Patent Literature 1.) In the selection method described in Patent Literature 1, a bending moment generated in the shaft during a swing of a golfer is calculated based on a bending amount measured by a strain gauge attached to the golf club, and with use of EI (bending rigidity) distribution of the shaft of the golf club calculated in advance and various other parameters of the golf club shaft, a deformation behavior of the shaft during the swing is analyzed. Furthermore, in the selection method described in Patent Literature 1, the deformation behavior obtained by the analysis is classified into a predetermined pattern, and a golf club shaft having EI distribution suitable for the golfer may be selected.

CITATION LIST

Patent Literature

Patent Literature 1: Japanese Patent Publication No. 4145618

SUMMARY OF INVENTION

Technical Problem

However, regarding the selection of a golf club suitable for a golf swing, there is room for further optimization in the method of analyzing the deformation behavior of the shaft during the golf swing based on the bending moment generated during the swing measured by means of the golf club attached with the strain gauge as in Patent Literature 1.

The present invention has been conceived in view of the above circumstances, and an objective of the present invention is to provide a golf swing classification method, a golf club selection method, a golf swing classification device, and a golf swing classification system that are capable of optimizing selection of a golf club.

Solution to Problem

A first aspect of the present invention for achieving the above objective resides in a golf swing classification method for classifying a golf swing when a golf club hits a golf ball, including the steps of: acquiring acceleration in at least a single point on the golf club or in at least one point that follows the single point during the golf swing; and mapping a behavior of the golf club based on a time period from a time point when an absolute value of the acceleration is at a maximum to a time point when the golf club hits the golf ball. According to the above classification method, the golf swing is classified based on the time period (which may be referred to below as a "bending return time period") from the time point when the absolute value of the acceleration in the at least a single point on the golf club or in the at least one point that follows the single point is at the maximum to the time point (which may be referred to below as an "impact time point") when the golf club hits the golf ball. As a result, the selection of a golf club is optimized.

A second aspect of the present invention resides in the golf swing classification method of the first aspect, preferably further including the step of: acquiring a maximum value of the acceleration generated in a head of the golf club prior to the time point when the golf club hits the golf ball during the golf swing, wherein in the step of mapping the behavior of the golf club, the maximum value of the acceleration generated in the head is mapped as the behavior of the golf club. With the above structure, the mapping is performed with use of the bending return time period and the maximum value of the acceleration generated in the head, the selection of a golf club is optimized by using a simple configuration.

A third aspect of the present invention resides in the golf swing classification method of the first aspect, preferably further including the step of: acquiring a maximum value of a bending amount generated in a shaft of the golf club prior to the time point when the golf club hits the golf ball during the golf swing, wherein in the step of mapping the behavior of the golf club, the maximum value of the bending amount generated in the shaft is mapped as the behavior of the golf club. With the above structure, since the mapping is performed with use of the bending return time period and the maximum value of the bending amount generated in the shaft, the selection of a golf club is further optimized.

A fourth aspect of the present invention resides in the golf swing classification method of the third aspect, preferably further including the step of: imaging the behavior of the head of the golf club during the golf swing by an image device that is attached to the golf club in a manner such that the image device is capable of imaging the head of the golf club, wherein the step of acquiring the maximum value of the bending amount generated in the shaft includes the step of calculating the maximum value of the bending amount based on the behavior of the head of the golf club imaged by the image device. With the above structure, since the maximum value of the bending amount of the shaft is calculated based on the behavior of the head imaged by the image device that is attached to the golf club in the manner such that the image device is capable of imaging the head, the maximum value of the bending amount of the shaft is acquired with improved precision. As a result, the selection of a golf club is further optimized.

A fifth aspect of the present invention resides in a golf club selection method, including the step of: selecting an optimal golf club for the golf swing in accordance with a result of classification according to the golf swing classification method of any one of the first to fourth aspects. According to the above selection method, the selection of a golf club optimal for the golf swing is optimized.

A sixth aspect of the present invention resides in a golf swing classification device that classifies a golf swing when a golf club hits a golf ball, including: an acceleration acquisition unit that acquires acceleration in at least a single point on the golf club or in at least one point that follows the single point during the golf swing; and a mapping unit that maps a behavior of the golf club based on a time period from a time point when an absolute value of the acceleration is at a maximum to a time point when the golf club hits the golf ball. According to the above classification device, the selection of a golf club optimal for the golf swing is optimized.

A seventh aspect of the present invention resides in a golf swing classification system for classifying a golf swing when a golf club hits a golf ball, including: an acceleration measuring device that measures acceleration in at least a single point on the golf club or in at least one point that follows the single point during the golf swing; and a classification device, wherein the classification device includes: an acceleration acquisition unit configured to acquire the acceleration measured by the acceleration measuring device; and a mapping unit configured to map a behavior of the golf club based on a time period from a time point when an absolute value of the acceleration is at a maximum to a time point when the golf club hits the golf ball. According to the above classification system, the selection of a golf club optimal for the golf swing is optimized.

An eighth aspect of the present invention resides in the golf swing classification system of the seventh aspect, further including: an image device attached to the golf club in a manner such that the image device is capable of imaging a head of the golf club, wherein the classification device further includes a bending amount acquisition unit configured to acquire a bending amount generated in a shaft of the golf club during the golf swing, the bending amount acquisition unit calculating a maximum value of the bending amount prior to the time point when the golf club hits the golf ball based on the behavior of the head of the golf club imaged by the image device, and the mapping unit maps, as the behavior of the golf club, the maximum value of the bending amount generated in the shaft of the golf club prior to the time point when the golf hits the golf ball as calculated by the bending-amount acquisition unit.8. With the above structure, the maximum amount of the bending amount of the shaft is acquired with more precision. As a result, the selection of a golf club is optimized.

Advantageous Effects of Invention

According to the present invention, the selection of a golf club suitable for the golf swing is optimized.

BRIEF DESCRIPTION OF THE DRAWING

The present invention will be further described below with reference to the accompanying drawings, wherein.

DESCRIPTION OF EMBODIMENTS

The following describes one embodiment of each of a golf swing classification method, a golf club selection method, a golf swing classification device, and a golf swing classification system according to the present invention in detail with reference to the drawings.

Figure 1:
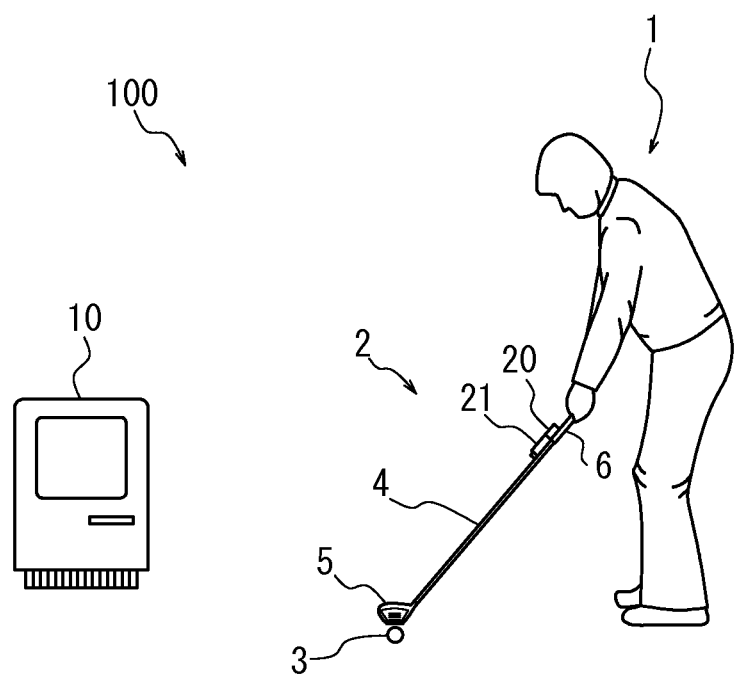
FIG. 1 illustrates a golf swing classification system according to one embodiment of the present invention.

FIG. 1 illustrates a golf swing classification system (which may be referred to below simply as a "classification system") according to one embodiment of the present invention. A classification system 100 has a function of classifying a golf swing when a golfer 1 hits a golf ball 3 with a golf club 2. The golf swing classification system 100 includes a golf swing classification device (which may be referred to below simply as a "classification device") 10 and an acceleration measurement device 20 attached to the golf club 2. Similarly to normal golf clubs, the golf club 2 includes a shaft 4, a head 5, and a grip 6.

The acceleration measurement device 20 is constituted by using an accelerometer, for example. The accelerometer measurement device 20 measures acceleration (which may be referred to below as "acceleration near the hand") in at least a single point in an upper portion of the golf club 2 or in at least one point that follows the single point (which may be referred to below as "near the hand of the golfer" or "near the hand") when the golfer 1 hits the golf ball 3 with the golf club 2. The at least a single point in the upper portion of the golf club 2 herein refers to, for example, a single point on the golf club 2 that is located in proximity to the grip 6 of the golf club 2, and refers to, for example, a single point on the grip 6 or a single point on the shaft 4 that is located within +300 mm, and preferably within +30 mm from an end portion of the grip 6 on the side of the shaft toward the direction of the head 5. When the grip 6 has a grip end (an end portion of the grip 6 on the opposite side to the shaft 4) whose section is inclined, a distance along a center axis line of the grip 6 may be a basis.

The at least one point that follows the at least single point in the upper portion of the golf club 2 refers to, for example, at least one point on the hand or on the arm of the golfer 1. To "follow the at least single point in the upper portion of the golf club 2" herein means to be displaced with a positional relation with respect to the at least single point remaining unchanged when the at least single point in the upper portion of the golf club 2 is displaced when the golfer 1 hits the golf ball 3 with the golf club 2 (during a golf swing). That is to say, for example, the acceleration measurement device 20 constituted by using the accelerometer may be attached directly to the grip 6 of the golf club 2, or may be attached to the hand, the wrist, and the arm or the golfer 1. Although in FIG. 1 the acceleration measurement device 20 is illustrated to be attached to the end portion of the grip 6 on the side of the shaft for clarification, as described above, the acceleration measurement device 20 may be disposed in any position in which the acceleration measurement device 20 is capable of measuring the acceleration at a single point on the grip 6 or at a single point on the shaft 4 that is located within +300 mm, and preferably within +30 mm from the end portion of the grip 6 on the side of the shaft toward the direction of the head 5, for example.

Preferably, the classification system 100 further includes an image device 21 that is attached to the golf club 2 in a manner such that the image device 100 is capable of imaging the head 5 of the golf club 2. The image device 21 images a behavior of the head 5 of the golf club 2 when the golfer 1 hits the golf ball 3 with the golf club 2. By doing so, displacement of the head 5 during a golf swing may be recorded, and the record may be also used by a bending amount acquisition unit 124 for calculation of a bending amount. The bending amount acquisition unit 124 is later described.

The "manner such that the image device 100 is capable of imaging" the head 5 of the golf club 2 refers to the manner in which the image device 100 is attached to the golf club 2 while being spaced apart from the head 5, which is displaced due to bending of the shaft 4 during a golf swing, a distance sufficient to allow the head 5 to be imaged without being framed out during the golf swing. The "manner such that the image device 100 is capable of imaging" refers to, for example, a manner in which the image device 100 is attached to the shaft 4 of the golf club 2 in a position on the shaft 4 that is located right under the end portion of the grip 6 on the side of the shaft or in proximity to the end portion of the grip 6 on the side of the shaft, e.g., a position within +300 mm, and preferably within +30 mm from the end portion of the grip 6 on the side of the shaft. Attaching the image device 21 to the golf club 2 in the aforementioned manner provides an advantage that the position of the image device 21 is unlikely to be affected by deformation of the golf club 2 during a golf swing and an advantage that an image of the head 5 covering a wide area may be obtained. Even when an optical axis of the image device 21 is not parallel with a shaft axis, there is no problem as long as the head 5 may be imaged throughout a golf swing. Furthermore, the image device 21 does not need to be always capable of imaging the entire head 5 throughout a golf swing, and the image device 21 only needs to be capable of imaging a predetermined single point on the head 5 (an identification feature such as a pattern drawn on the head 5 or a marker provided on the head 5) that can be used for detection of displacement of the head 5.

The image device 21 is configured by using, for example, a digital high speed camera or a wireless camera. A frame rate of the camera may be appropriately selected in accordance with a golf swing speed and may be 30 fps (frame per sec), for example. When the swing speed of the golfer 1 is high, the frame rate is preferably 200 fps or more, more preferably 240 fps or more, and most preferably 1000 fps or more. Preferably, the image device 21 is configured to be light weighted enough to allow the golfer 1 to execute a normal golf swing with use of the golf club 2.

Figure 2:
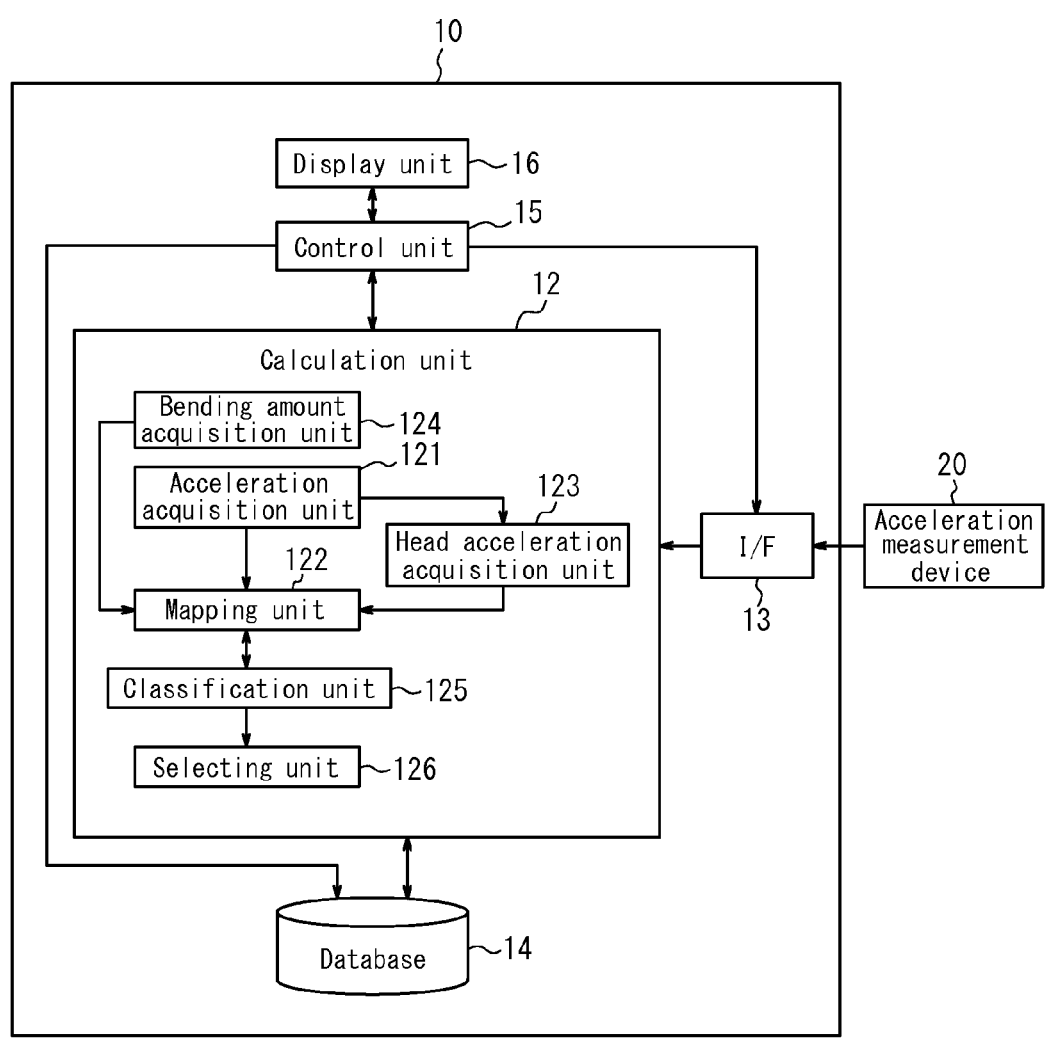
FIG. 2 illustrates a schematic configuration of a golf swing classification device according to one embodiment of the present invention.

As illustrated in FIG. 2, for example, the classification device 10 includes a calculation unit 12 constituted by using a CPU (Central Processing Unit) and a DSP (Digital Signal Processor). The classification device 10 also includes an acceleration acquisition unit 121 and a mapping unit 122 that are provided in the calculation unit 12.

The acceleration acquisition unit 121 acquires acceleration (acceleration near the hand) generated in the at least a single point in the upper portion of the golf club 2 or in the at least one point that follows the single point (near the hand of the golfer). Specifically, the acceleration acquisition unit 121 acquires acceleration data measured by the acceleration measurement device 20 via an interface (I/F) 13. Then, the acceleration acquisition unit 121 calculates a time period (a bending return time period) from a time point when an absolute value of the acceleration near the hand of the golfer (in FIG. 1, the single point on the grip 6 of the golf club 2 where the acceleration is measured by the acceleration measurement device 20) is at a maximum to a time point when the golf club 2 hits the golf ball 3. The time point (an impact time point) when the golf club 2 hits the golf ball 3 may be determined according to changes in the acceleration near the hand, for example, by the fact that the acceleration near the hand is changed due to impact occurring when the golf club 2 hits the golf ball 3. Simply, the impact time point may also be a time point when the value of acceleration measured by the acceleration measurement device 20 is at a minimum.

Figure 3:
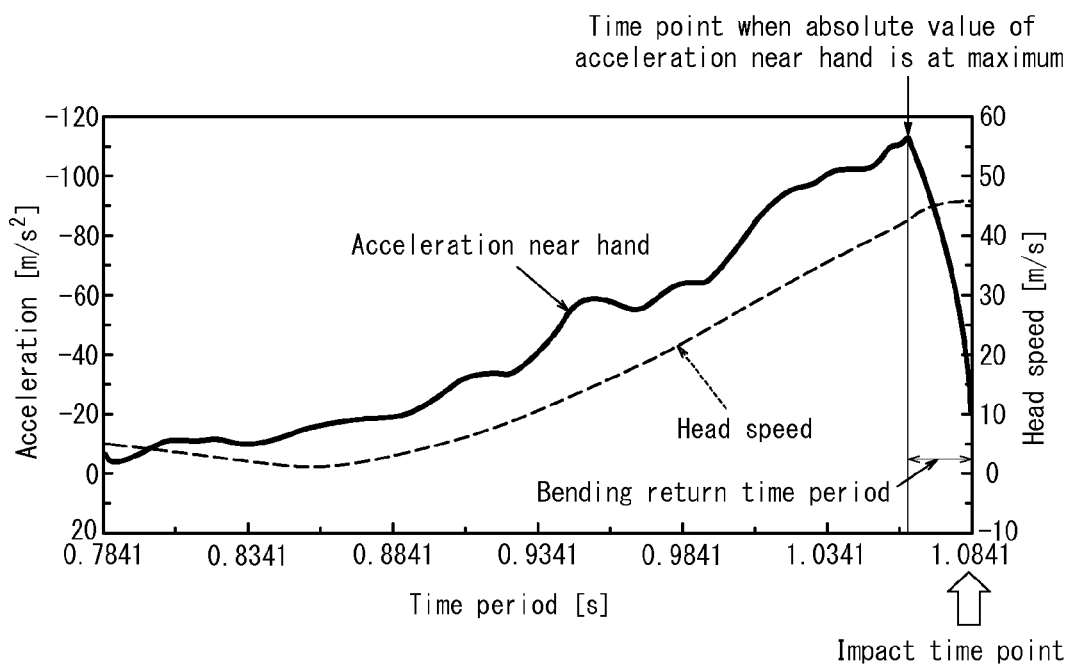
FIG. 3 illustrates one example of temporal changes in acceleration near the hand acquired by a golf swing classification system according to one embodiment of the present invention.

The mapping unit 122 maps the behavior of the golf club 2 based on the time period (the bending return time period) from the time point when the absolute value of the acceleration near the hand is at the maximum to the time point when the golf club 2 hits the golf ball 3. The "mapping" herein refers to plotting of the bending return time period and indices indicating other behaviors of the golf club (e.g. maximum value of the acceleration of the head or of the bending amount) that have been calculated for a certain golf swing, with the bending return time period as the basis. FIG. 3 illustrates one example of measurement data of the acceleration near the hand. FIG. 3 illustrates acceleration measured at the grip end of the grip 6 as the acceleration near the hand. Providing that a direction of movement of swing is considered to be plus, a direction of the acceleration of the grip end is opposite to the above direction and is denoted with a minus sign.

As is clear from FIG. 3, the acceleration near the hand measured by the acceleration measurement device 20 gradually increases so that the absolute value thereof is at the maximum prior to the impact time point and suddenly decreases toward the impact time point right after the absolute value reaches the maximum. The present inventors have found that there are individual differences among golfers in the time period (the bending return time period) from the time point when the absolute value of the acceleration near the hand is at the maximum to the impact time point. By mapping the behavior of the golf club with use of the bending return time period, a favorable mapping result is obtained.

As illustrated in FIG. 3, although the maximum value of the acceleration near the hand reaches the maximum at a time point prior to the impact, the head speed of the golf club increases toward the impact time point.

Preferably, the mapping unit 122 also maps, as the behavior of the golf club 2, the maximum value of the absolute value of the acceleration generated in the head 5 of the golf club 2 and the maximum value of the bending amount generated in the shaft 4 of the golf club 2 during a golf swing. Accordingly, the classification device 10 preferably includes a head acceleration acquisition unit 123 or a bending amount acquisition unit 124.

The aforementioned values indicating the behaviors of the golf club 2, such as the maximum value of the head acceleration and the maximum value of the bending amount of the shaft, are stored in the golf club 2 prior to the impact time point during a golf swing and may serve as indices of magnitude of force that contributes to improvement of the head speed at the impact time point and around the impact time point. That is to say, when the values are high, this leads to a probability that force of a large magnitude will be applied to the head 5 of the golf club 2 at the impact time point or around the impact time point.

In the present invention, by mapping the aforementioned values with the bending return time period as the basis, a relation between the magnitude of force applied to the head 5 and a time length required from when the force is applied to the impact may also be manifested. In contrast to the present invention, conventionally, although it has been attempted to analyze a golf swing by using only the magnitude of force such as the head speed and the bending amount applied to the head 5 as the index, the time length (the bending return time period) from when the force is applied to the impact was not paid attention to. Accordingly, when two subjects A and B who generate the same bending amount during a swing are assumed, even when the subject A tends to apply force by which the absolute value of the acceleration near the hand reaches the maximum and by which the head speed is improved with respect to the head at a time point closer to the impact time point than the subject B (i.e. when the bending return time period of the subject A is shorter), it was difficult to distinguish the golf swing of the subject A over the golf swing of the subject B. On the other hand, according to the present invention, since the values indicating the behavior of the golf club 2 are mapped with the bending return time period as the basis, the subject A and the subject B are distinguished. As a result, the present invention makes it possible to select respective golf clubs suitable for the subjects A and B.

The head acceleration acquisition unit 123 acquires the maximum value of acceleration generated in the head 5 of the golf club 2 prior to the time point when the golf club 2 hits the golf ball 3 during a golf swing. Specifically, the head acceleration acquisition unit 123 assumes the golf club 2 as a rigid body from data of the acceleration near the hand of the golfer 1 that has been measured by the acceleration measurement device 20 and that has been acquired by the acceleration acquisition unit 121. With use of at least a length of the golf club 2 (a distance from the position at which the data of the acceleration near the hand is measured, that is to say, the position of the acceleration measurement device 20, to the barycenter of the head 5 of the golf club 2) and the direction of the shaft axis during the swing, the head acceleration acquisition unit 123 may calculate acceleration at the barycenter of the head of the golf club and may acquire the maximum value of the acceleration. The head acceleration acquisition unit 123 may also be configured to acquire the head acceleration by using any known simulation method, such as the multibody dynamics theory or the like.

The bending amount acquisition unit 124 acquires the maximum value of bending amount (a maximum bending amount) generated in the shaft 4 of the golf club 2 prior to the time point when the golf club 2 hits the golf ball 3 during a golf swing. The bending amount acquisition unit 124 calculates the bending amount of the shaft 4 based on the behavior of the head 5 of the golf club 2 imaged by the image device 21 included in the classification system 100. The following describes a method for calculation of the bending amount by the bending amount acquisition unit 124. In the description, it is assumed that the head 5 of the golf club 2 is provided with the identification feature formed by a circle marker.

Figure 4:
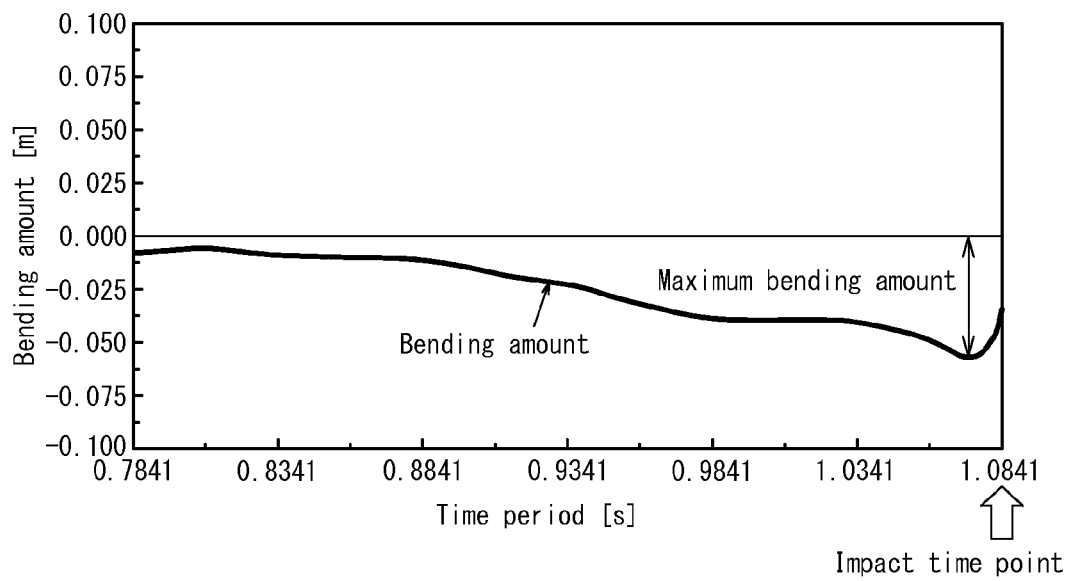
FIG. 4 illustrates one example of temporal changes in bending amount acquired by a golf swing classification system according to one embodiment of the present invention.

Firstly, the bending amount acquisition unit 124 extracts optional image data from image data of the head 5 during a golf swing. The bending amount acquisition unit 124 also extracts, for the extracted image data, an identification feature by using the circle fitting method or the like and acquires center position coordinates of the extracted identification feature. The acquired coordinates are coordinates on a virtual projection plane that is uniquely determined for the image data imaged by the image device 21. The bending amount acquisition unit 124 acquires the bending amount of the shaft 4 based on temporal changes in the coordinates of the center position of the identification feature on the virtual projection plane. FIG. 4 illustrates one example of the temporal changes in the bending amount of the shaft 4 obtained by the bending amount acquisition unit 124. In FIG. 4, a state with the bending amount being zero refers to a state where the shaft 4 is not bent at all. The bending amount when the shaft 4 is bent in the opposite direction to the movement of golf swing is indicated by a minus sign, and the bending amount when the shaft 4 is bent in the direction of the movement of golf swing is indicated by a plus sign.

For example, the bending amount acquisition unit 124 may calculate a maximum value of a direct distance between the center position coordinates of the identification feature before or when a golf swing is started and the center position coordinates of the identification feature during the golf swing on the virtual projection plane and as the maximum value of the bending amount generated in the shaft 4 prior to the time point when the golf club 2 hits the golf ball 3. More particularly, the bending amount acquisition unit 124 may resolve components of the bending amount in the direction of the movement of golf swing and in a direction perpendicular to the direction of the movement and calculate a maximum value obtained for one of the directions as the maximum value of the bending amount generated in the shaft 4. Alternatively, the mapping unit 122 may use the two values obtained by resolving the components of the bending amount in the direction of the movement of golf swing and in the direction perpendicular to the direction of the movement, and the bending return time period, for mapping on XYZ space. With such mapping, the mapping unit 122 is able to map the golf swing in more details, resulting in further optimization of the selection of a golf club.

Of course, it is possible to provide the bending amount acquisition unit 124 with a simulation function and configure the bending amount acquisition unit 124 to calculate, for a the golf club set as the elastic body in a simulation model, the bending amount from the data of the acceleration near the hand of the golfer 1 acquired by the acceleration measurement device 20.

Figure 5:
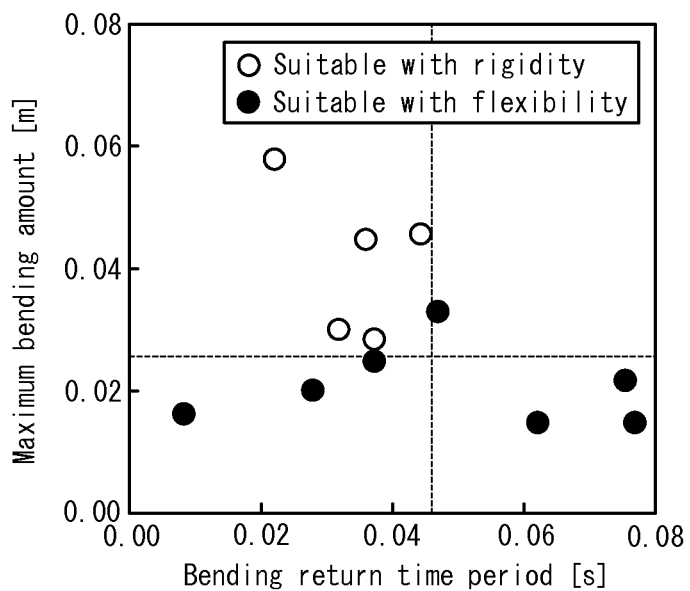
FIG. 5 illustrates one example of a result of mapping performed by a golf swing classification system according to one embodiment of the present invention.

FIG. 5 illustrates one example of a result of mapping of the maximum values of the bending amount (the maximum bending amounts) generated in the shaft 4 as calculated above with respect to the bending return time periods. In FIG. 5, the horizontal axis represents the bending return time period, and the vertical axis represents the maximum bending amount. Each of data points basically denotes data calculated from swing data of a golf swing executed by one golfer.

Preferably, the classification device 10 includes a classification unit 125. The classification unit 125 classifies a golf swing in accordance with the result of mapping performed by the mapping unit 122. For example, the classification unit 125 determines which one of a plurality of regions defined in advance on the mapping space the swing data corresponds to. In the mapping space, the horizontal axis represents the bending return time period, and the vertical axis represents the behavior of the golf club. Alternatively, when the number of mapped samples (number of swing data pieces) is greater than or equal to a predetermined number, the classification unit 125 may classify the golf swings by means of threshold detection, clustering, or the like.

For example, by means of the threshold detection, the classification unit 125 is capable of classifying subjects into a subject who would improve the head speed by using a rigid golf club (having a high frequency) and a subject who would improve the head speed by using a flexible golf club (having a small frequency).

The phrase "suitable with rigidity" in FIG. 5 refers to a subject who would improve the head speed by using a rigid golf club (having a high frequency), and "suitable with flexibility" refers to a subject who would improve the head speed by using a flexible golf club (having a small frequency). By using a plurality of virtual golf club models in which rigidity distribution remains unchanged and the frequency is varied in the simulation, the present inventors input data of the acceleration near the hand of various subjects during the golf swings and detected influence caused by the frequency of the golf club on the head speed of the subjects. As a result, it has been found that, depending on types of the golf swings of the subjects, in some cases the head speed is improved when the frequency of the golf club is low, and in other cases the head speed is improved when the frequency of the golf club is high. When classifying the subjects into a subject "suitable with rigidity" and a subject "suitable with flexibility", the present inventors found it effective to map the maximum values of the acceleration generated in the head 5 or the maximum values of the bending amount generated in the shaft 4 as the behaviors of the golf club with respect to the bending return time periods. The reason is that, depending on how rigid the shaft 4 is, the influence caused by force applied to the head of the golf club during the bending return time period (e.g. the maximum value of the acceleration generated in the head 5 or the maximum value of the bending amount generated in the shaft 4) on the head speed is varied.

When the classification unit 125 is configured to classify subjects into a subject "suitable with rigidity" and a subject "suitable with flexibility" by the threshold detection, a threshold predetermined according to any method may be used, for example.

Preferably, the classification device 10 includes a selection unit 126 that selects a golf club. The selection unit 126 has a function of selecting an optimal golf club for a golf swing based on a result of classification according to the classification method employed by the classification device 10. Specifically, the selection unit 126 selects a result of classification performed by the classification unit 125 and a golf club suitable for the corresponding one of the classification categories stored in database 14 in advance. A control unit 15 may control a display unit 16 to display the result of selection performed by the selection unit 126 on the display unit 16. Of course, the control unit 15 may also control the display unit 16 to display, on the display unit 16, the behavior of the head imaged by the image device 21 and a result of classification performed by the classification unit 125.

It is obvious to a skilled person that a number of modifications and substitutions are possible within the concept and scope of the present invention. Accordingly, the present invention should not be understood to be limited to the embodiment described above, and various modifications and changes are possible without departing from the scope of the claims.

Figure 6:
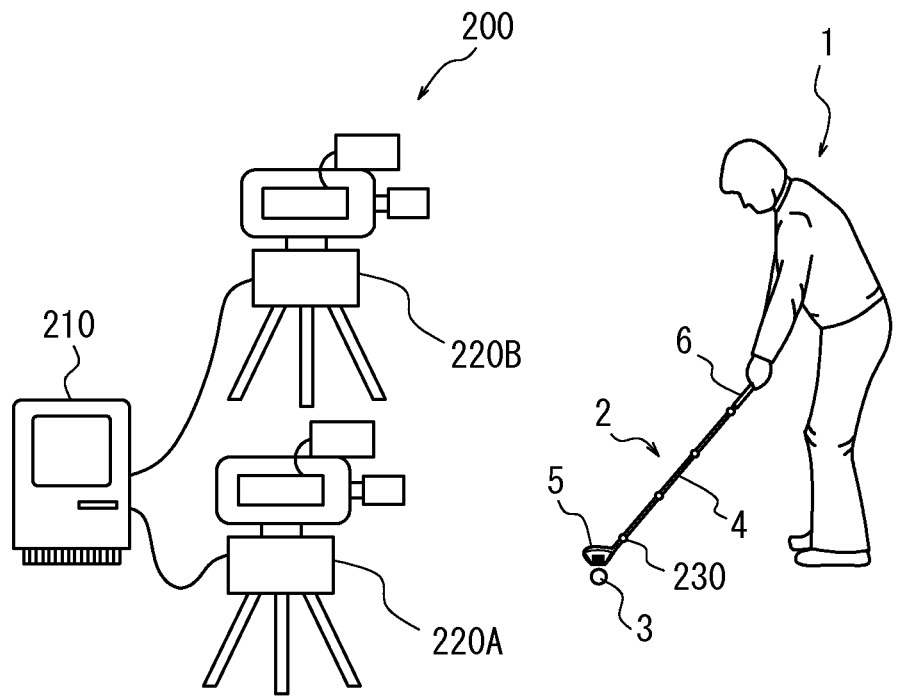
FIG. 6 illustrates a golf swing classification system according to one modified example of the present invention.

For example, in the classification system according to the present invention, the acceleration measurement device may be configured by using a stereo camera. FIG. 6 illustrates a classification system 200 in which the acceleration measurement device is configured by using a first camera 220A and a second camera 220B. In the present modified example, the acceleration measurement device is configured by using the first camera 220A and the second camera 220B, and the golf club 2 is provided with a marker 230. The marker 230 may be, for example, a light-weight material such as styrene foam, a reflective tape, or the like. Other points in the structure are substantially the same as the above embodiment except for that the acceleration measurement device 20 and the image device 21 are not provided.

The first camera 220A and the second camera 220B are, for example, digital high-speed cameras or high-speed video cameras constituting a motion capture system and are capable of imaging an object in frequent motion with high sensitivity. The frame rate of the first camera 220A and the second camera 220B when imaging a golf swing is 160 fps, for example. The number of the marker 230 provided on the shaft 4 of the golf club 2 is any and may be four, for example.

The acceleration acquisition unit included in the classification device 210 acquires time series data of the acceleration near the hand of the golfer 1 from images of the marker 230 during a swing of the golfer 1 that are imaged by the first camera 220A and the second camera 220B. The bending amount acquisition unit included in the classification device 210 acquires the maximum value of the bending amount generated in the shaft 4 of the golf club 2 during the swing from the images of the marker 230 imaged during the swing. The mapping unit included in the classification device 210 executes mapping as in the first embodiment. In this way, configuring the acceleration measurement device by using a stereo camera omits the need for providing the acceleration measurement device 20 and the image device 21 in the golf club 2. As a result, the weight of the golf club 2 that the golfer 1 uses is further approximated to the weight in a normal condition, and data of a normal golf swing of the golfer 1 may be acquired.

REFERENCE SIGNS

1: golfer
2: golf club
3: golf ball
4: shaft
5: head
6: grip
10, 210: classification device
12: calculation unit
13: interface (I/F)
14: database
15: control unit
16: display unit
20: acceleration measurement device
21: image device
100, 200: classification system
121: acceleration acquisition unit
122: mapping unit
123: head acceleration acquisition unit
124: bending amount acquisition unit
125: classification unit
126: selecting unit
220A, 220B: camera
230: marker

The invention claimed is:
1. A golf club selection method, comprising:
acquiring acceleration in at least a single point on the golf club or in at least one point that follows the single point during the golf swing;
mapping a behavior of the golf club based on a maximum value of the acceleration generated in a head of the golf club, prior to the time point when the golf club hits the golf ball during the golf swing, and a bending return time period, the bending return time period being a time period from a time point when an absolute value of the acceleration is at a maximum to a time point when the golf club hits the golf ball;

classifying the golf swing based on a result of the mapping;

selecting an optimal golf club having optimal shaft rigidity for the golf swing in accordance with a result of the classifying; and imaging the behavior of the head of the golf club during the golf swing by an image device that is attached to the golf club in a manner such that the image device is capable of imaging the head of the golf club, wherein the acquiring the maximum value of the bending amount generated in the shaft includes calculating the maximum value of the bending amount based on the behavior of the head of the golf club imaged by the image device.

2. The golf club selection method of claim 1, wherein during the selecting, the optimal golf club is selected such that a head speed can be improved.

3. The golf club selection method of claim 1, wherein during the selecting, the optimal golf club is selected based on the result of the classifying and on a frequency of the golf club.

4. A golf club selection device comprising:

an acceleration acquisition unit configured to acquire acceleration in at least a single point on the golf club or in at least one point that follows the single point during a golf swing;

a mapping unit configured to map a behavior of the golf club based on a maximum value of the acceleration generated in a head of the golf club, prior to the time point when the golf club hits the golf ball during the golf swing, and a bending return time period, the bending return time period being a time period from a time point when an absolute value of the acceleration is at a maximum to a time point when the golf club hits the golf ball;

a classification unit configured to classify the golf swing based on a result of the mapping;

a selecting unit configured to select an optimal golf club having optimal shaft rigidity for the golf swing in accordance with a result of the classifying by the classification unit; and an imaging unit configured to image the behavior of the head of the golf club during the golf swing, the imaging unit attached to the golf club in a manner such that the imaging unit is capable of imaging the head of the golf club, wherein the acceleration acquisition unit is configured to acquire the maximum value of the bending amount generated in the shaft by calculating the maximum value of the bending amount based on the behavior of the head of the golf club imaged by the imaging unit.

5. A golf club selection system, comprising:

an acceleration measuring device configured to measure acceleration in at least a single point on the golf club or in at least one point that follows the single point during a golf swing;

a classification device, wherein the classification device includes:

an acceleration acquisition unit configured to acquire the acceleration measured by the acceleration measuring device;

a bending amount acquisition unit configured to acquire a bending amount generated in a shaft of the golf club during the golf swing, the bending amount acquisition unit calculating a maximum value of the bending amount prior to the time point when the golf club hits the golf ball based on the behavior of the head of the golf club imaged by the image device; and a mapping unit configured to map a behavior of the golf club based on a maximum value of the acceleration generated in a head of the golf club, prior to the time point when the golf club hits the golf ball, and a bending return time period, the bending return time period being a time period from a time point when an absolute value of the acceleration is at a maximum to a time point when the golf club hits the golf ball, the classification device configured to classify the golf swing based on a result of the mapping by the mapping unit;

a selection device configured to select an optimal golf club having optimal shaft rigidity for the golf swing in accordance with a result of the classifying by the classification unit; and an imaging device configured to image the behavior of the head of the golf club during the golf swing, the imaging device attached to the golf club in a manner such that the image device is capable of imaging the head of the golf club, wherein the acceleration acquisition unit is configured to acquire the maximum value of the bending amount generated in the shaft by calculating the maximum value of the bending amount based on the behavior of the head of the golf club imaged by the imaging device.

6. The golf club selection system of claim 5, further comprising:

an image device attached to the golf club in a manner such that the image device is capable of imaging a head of the golf club.

7. The golf club selection system of claim 5, wherein the acceleration measuring device is positioned at a single point on the grip or at least a single point on the shaft that is located within +300 mm from an end portion of the grip on the side of the shaft toward the direction of the head.

* * * * *